United States Patent
Suzuki et al.

(10) Patent No.: US 11,808,670 B2
(45) Date of Patent: Nov. 7, 2023

(54) IMMUNOCHROMATOGRAPHIC DEVICE

(71) Applicant: TANAKA KIKINZOKU KOGYO K.K., Tokyo (JP)

(72) Inventors: Keita Suzuki, Hiratsuka (JP); Yuya Kato, Hiratsuka (JP); Hisahiko Iwamoto, Hiratsuka (JP)

(73) Assignee: TANAKA KIKINZOKU KOGYO K.K., Tokyo (JP)

(*) Notice: Subject to any disclaimer, the term of this patent is extended or adjusted under 35 U.S.C. 154(b) by 1365 days.

(21) Appl. No.: 16/081,984

(22) PCT Filed: Mar. 3, 2017

(86) PCT No.: PCT/JP2017/008624
§ 371 (c)(1),
(2) Date: Aug. 12, 2019

(87) PCT Pub. No.: WO2017/150733
PCT Pub. Date: Sep. 8, 2017

(65) Prior Publication Data
US 2020/0225198 A1 Jul. 16, 2020

(30) Foreign Application Priority Data
Mar. 4, 2016 (JP) .................. 2016-042707

(51) Int. Cl.
| | |
|---|---|
| *G01N 33/569* | (2006.01) |
| *G01N 33/543* | (2006.01) |
| *B01J 20/286* | (2006.01) |
| *G01N 30/02* | (2006.01) |
| *B01J 20/292* | (2006.01) |

(52) U.S. Cl.
CPC ...... *G01N 33/56944* (2013.01); *B01J 20/286* (2013.01); *G01N 33/543* (2013.01); *B01J 20/292* (2013.01); *G01N 2030/027* (2013.01)

(58) Field of Classification Search
None
See application file for complete search history.

(56) References Cited

U.S. PATENT DOCUMENTS

| | | |
|---|---|---|
| 5,536,646 A | 7/1996 | Sand et al. |
| 2008/0206849 A1* | 8/2008 | Zak .............. G01N 33/558 435/287.2 |
| 2009/0203155 A1* | 8/2009 | Chiku ............ G01N 33/54386 530/391.5 |
| 2011/0008909 A1 | 1/2011 | Homrig et al. |
| 2015/0010918 A1 | 1/2015 | Ruvinsky |
| 2016/0370368 A1* | 12/2016 | Kato .............. G01N 33/54393 |

FOREIGN PATENT DOCUMENTS

| | | | |
|---|---|---|---|
| EP | 0280557 A2 | 8/1988 | |
| EP | 3032260 A1 | 6/2016 | |
| EP | 3324185 A1 | 5/2018 | |
| JP | 07-503543 A | 4/1995 | |
| JP | 2008-509384 A | 3/2008 | |
| JP | 3166728 U | 3/2011 | |
| JP | 2015-034719 A | 2/2015 | |
| JP | 2015034719 A * | 2/2015 | ......... G01N 33/5306 |
| WO | WO 2015/147291 A1 | 10/2015 | |

OTHER PUBLICATIONS

PCT, International Search Report for PCT/JP2017/008624, dated May 30, 2017.
EP, Extended European Search Report for 17760195.2, dated Dec. 4, 2018.
JP, Office Action for Japanese application No. 2016-042707, dated Jun. 25, 2019.

* cited by examiner

*Primary Examiner* — Jana A Hines
*Assistant Examiner* — Khatol S Shahnan Shah
(74) *Attorney, Agent, or Firm* — Foley & Lardner LLP

(57) ABSTRACT

The invention relates to an immunochromatographic device which contains a nitrous acid compound and an organic acid or an organic acid derivative and which is for detecting a detection target in an analyte wherein a sample droplet-receiving member, a labeling substance-holding member, a chromatography medium member and an absorption member are arranged in a manner that a sample develops in this order and wherein a part containing the nitrous acid compound and a part containing the organic acid or the like are at upstream positions from the labeling substance-containing part, and the part containing the nitrous acid compound and the part containing the organic acid or the like are not substantially in contact with each other in the thickness direction.

5 Claims, 4 Drawing Sheets

IMMUNOCHROMATOGRAPHIC DEVICE

TECHNICAL FIELD

An immunochromatographic device, an immunochromatographic kit and an immunochromatographic detection method which are highly important for a simple external diagnostic kit or a mobile diagnostic device for detecting a detection target in an analyte are described.

BACKGROUND ART

Recently, an immunoassay of the strip type for immunochromatography has an increasing versatility as a simple external diagnostic kit or a mobile diagnostic device for detecting a detection target in an analyte using the specific reactivity of an antibody.

In particular, there is now enhanced interest in simple test devices for testing the presence or absence of infection with a pathogen such as influenza viruses and bacteria based on an immunochromatographic method, and the test devices have been studied and developed.

Diagnosis of hemolytic streptococcal (to be also referred to as streptococcal) infection is made through a test using a group-specific polysaccharide as an antigen. Although methods using an enzyme, a bacteriophage, hydrochloric acid, hypochlorous acid and the like are known as methods for extracting the polysaccharide, an extraction method using nitrous acid is the most common method.

Advantages of the extraction method using nitrous acid are that the extraction efficiency of the polysaccharide is high and that nitrous acid is inexpensive and easy to handle. However, one of its disadvantages is that nitrous acid has to be prepared each time by mixing a nitrous acid compound such as sodium nitrite and an organic acid such as acetic acid before the extraction because nitrous acid itself is an unstable compound that is easily decomposed.

Preparing nitrous acid each time is a heavy burden to doctors, laboratory technicians and the like when they constantly make diagnoses. In addition, because a mixing step is included, a correct and safe diagnosis may not always be made due to a mistake in mixing the reagents or the like.

To overcome the problems, simple test devices which simplify the step of extracting a polysaccharide antigen from a hemolytic *Streptococcus* have also been studied and developed.

For example, Patent Literature 1 proposes a simplified method for extracting a polysaccharide antigen from an organism (especially group A or group B streptococci) using a kit comprising in packaged combination a) a first absorbent material which has been impregnated with a premeasured amount of a nitrite salt and dried, b) a second absorbent material which has been impregnated with premeasured amounts of a neutralizing base and buffer and dried and c) a premeasured amount of an aqueous solution of an acid (see Patent Literature 1).

Some analytical devices and methods for detecting a carbohydrate antigen which is characteristic of a microorganism/bacterial organism such as those of the family Streptococcaceae are already sold on the market. For example, QuickVue DipStick Strep A (DS Pharma Biomedical Co., Ltd.), Strep A TestPack Plus OBC (Sanwa Kagaku Kenkyusho Co., Ltd.) and the like are immunochromatography reagents, and A Strept AD "Seiken" (Denka Seiken Co., Ltd.) and the like are known reagents for the slide latex agglutination method.

Here, in general, in order to conclude that a test of an analyte is positive using a commercial immunochromatography reagent, a hemolytic streptococcal concentration of $1\times10^6$ CFU/mL or more is required in the direct method.

Therefore, when the hemolytic streptococcal concentration is less than $1\times10^6$ CFU/mL, the following problems arise: a negative result is produced even though the test in reality is positive; the line observed in a positive case is not clear because an immunochromatography reagent that is obtained by labeling an antibody with an insoluble carrier is generally less sensitive than the enzyme immunoassay (EIA); and a positive result is produced even though the substance to be detected (an antigen or the like) is not contained in the sample solution, that is, a so-called false positive is caused.

Moreover, in an immunochromatographic method using an antibody labeled with an insoluble carrier (such as colloidal gold particles and colored latex particles), the insoluble carrier is sometimes agglutinated and causes nonspecific reaction depending on the measured sample, the measurement environment, the measurement conditions and the like, and the problems such as the slow development speed cannot always be solved.

Accordingly, for the immunochromatographic method in which various measurement samples, measurement environments and measurement conditions are applied, a test agent which does not cause the agglutination of the insoluble carrier and the nonspecific reaction and which has a high development speed has been studied.

To solve the above problems, the present inventors have developed a test agent containing a cyclic oligosaccharide and/or a nitrite in the sample extraction solution or the test device to be used for testing a bacterium with an immunochromatographic method (see Patent Literature 2).

The test agent does not cause the nonspecific reaction, which is induced when a protein component or the like in the analyte or in the immunochromatographic device is denatured/deposited and trapped at the determination line, even when the pH conditions of the development solution which is the sample extraction solution change during the development in the test device due to the held organic acid or nitrous acid generated during the test. Moreover, the test agent does not cause the agglutination of the antibody-immobilized particle colloids. The test agent thus has high test accuracy and a high development speed.

In the test device, nitrous acid can be generated in the presence of a cyclic oligosaccharide on the test device, instead of preparing nitrous acid at the time of each use, and thus the test efficiency, the test accuracy and the power saving property can be improved.

BACKGROUND ART LITERATURE

Patent Literatures

Patent Literature 1: JP-T-H7-503543
Patent Literature 2: JP-A-2015-34719

SUMMARY OF INVENTION

Technical Problem

However, it was found that the test device above requires improvements as follows in view of its storage stability.

It was found that, in the conventional test device containing an organic acid and a nitrite, the organic acid and the nitrite may partially diffuse in the test device, thus come into contact with each other and generate nitrous acid during the storage of the test device. When the generation of nitrous acid progresses during the storage of the test device, nitrous acid is not generated sufficiently during the actual use of the test device, and the extraction efficiency of the detection target and the detection sensitivity decrease. Thus, there is room for improvement in the storage stability of the test device in this regard.

Although the cyclic oligosaccharide contained in the test device is required for stabilizing the nitrite, the cyclic oligosaccharide is a viscous substance and thus is apt to cause a false positive depending on the measured sample and the measurement environment. Therefore, a method which can stabilize the nitrite during the storage of the device without using any cyclic oligosaccharide is also desired.

Accordingly, an object of the present invention and a problem to be solved by the present invention are to provide an immunochromatographic device and an immunochromatographic kit which have improved storage stability and which can detect a detection target with high sensitivity and an immunochromatographic detection method using the same.

In particular, an object and a problem are to inhibit the generation of nitrous acid during the storage of the device in an immunochromatographic device which contains a nitrous acid compound and an organic acid or an organic acid derivative and which is for detecting a detection target in an analyte and thus provide an immunochromatographic device and an immunochromatographic kit which have improved storage stability and an immunochromatographic detection method using the same.

Moreover, an object and a problem are to increase the efficiency of generation of nitrous acid during the use of an immunochromatographic device by improving the storage stability of the device and thus provide an immunochromatographic device and an immunochromatographic kit which can each detect a detection target with high sensitivity and an immunochromatographic detection method using the same.

Means for Solving Problems

The inventors of the present invention have conducted intensive studies to solve the problems. As a result, by positioning a part containing a nitrous acid compound and a part containing an organic acid or an organic acid derivative in specific arrangement in an immunochromatographic device which contains a nitrous acid compound and an organic acid or an organic acid derivative and which is for detecting a detection target in an analyte, the generation of nitrous acid during the storage of the device, which is caused when the nitrous acid compound and the organic acid or the organic acid derivative diffuse in the device and come into contact with each other, could be inhibited, and an immunochromatographic device with excellent storage stability could be provided.

That is, the present invention is as follows.

1. An immunochromatographic device for detecting a detection target in an analyte which includes a sample droplet-receiving member, a labeling substance-holding member having a labeling substance-containing part, a chromatography medium member having a detection part and an absorption member and which contains a nitrous acid compound and an organic acid or an organic acid derivative, wherein the sample droplet-receiving member, the labeling substance-holding member, the chromatography medium member and the absorption member are arranged in a manner that a sample develops in this order, the immunochromatographic device has a part containing the nitrous acid compound and a part containing the organic acid or the organic acid derivative at upstream positions from the labeling substance-containing part, and the part containing the nitrous acid compound and the part containing the organic acid or the organic acid derivative are not substantially in contact with each other in the thickness direction.

2. The immunochromatographic device according to 1, wherein the organic acid or the organic acid derivative is a nitrogen-containing heterocyclic compound represented by the following formula (1),

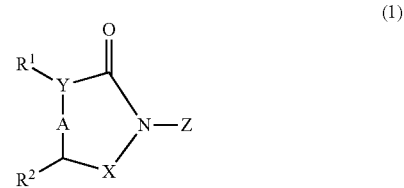

wherein in the formula (1), $R^1$ and $R^2$ each independently represents a hydrogen atom, a carbonyl group or an alkyl group which may have a substituent, wherein alkyl groups may bind to each other to form a ring and form an alicyclic hydrocarbon ring or an aromatic hydrocarbon ring, A represents a single bond or a double bond, X represents —C(=O)— or —(CH$_2$)$_n$—, Y represents a carbon atom or a nitrogen atom, n is 1 or 2, and Z represents a hydrogen atom, a hydroxyl group, an alkyl group which may have a substituent, —C(=O)$R^3$ or —O—C(=O)$R^3$, wherein $R^3$ represents an alkyl group which may have a substituent or an alkoxy group.

3. The immunochromatographic device according to 1 or 2, wherein the organic acid or the organic acid derivative is at least one selected from the group consisting of phthalimide, N-acetylphthalimide, N-(tert-butoxycarbonyloxy)phthalimide, N-hydroxysuccinimide, N-acetoxysuccinimide and hydantoin.

4. The immunochromatographic device according to any one of 1 to 3, wherein the nitrous acid compound is a nitrite.

5. The immunochromatographic device according to any one of 1 to 4, wherein the detection target is a Gram-positive bacterium.

6. The immunochromatographic device according to 5, wherein the Gram-positive bacterium is a hemolytic *Streptococcus*.

7. An immunochromatographic kit including the immunochromatographic device according to any one of 1 to 6 and an analyte dilution solution for diluting and developing the analyte.

8. An immunochromatographic detection method for detecting a detection target in an analyte using the immunochromatographic kit according to 7, including the following steps (i) to (v), (i) a step of dropping an analyte-containing solution obtained by diluting the analyte with the analyte dilution solution to the sample droplet-receiving member, (ii) a step of extracting a substance to be detected from the detection target in the analyte with nitrous acid generated through reaction of the nitrous acid compound and the organic acid or the organic acid derivative, (iii) a step of labeling the substance to be detected in the labeling substance-holding member, (iv) a step of allowing the analyte-containing solution to move on the chromatography medium member and detecting the detection target in the detection part, and (v) a step of absorbing the analyte-containing solution with the absorption member.

Effects of Invention

In the present invention, because a part containing a nitrous acid compound and a part containing an organic acid or an organic acid derivative are in specific arrangement in an immunochromatographic device which contains a nitrous acid compound and an organic acid or an organic acid derivative and which is for detecting a detection target in an analyte, the generation of nitrous acid during the storage of the device, which is caused when the organic acid or the organic acid derivative and the nitrous acid compound diffuse in the device and come into contact with each other, can be inhibited, and an immunochromatographic device and an immunochromatographic kit which have excellent storage stability and an immunochromatographic detection method using the device or the kit can be provided.

As described above, in the present invention, because the generation of nitrous acid during the storage of the device can be inhibited, the efficiency of generation of nitrous acid during the use of the device or the kit of the present invention can be increased, and the detection target can be detected with high sensitivity.

BRIEF DESCRIPTION OF DRAWINGS

FIG. 3A to FIG. 3D are cross sections for explaining partial structures of the immunochromatographic devices of embodiments of the present invention and the like.

DESCRIPTION OF EMBODIMENTS

Figure 1:
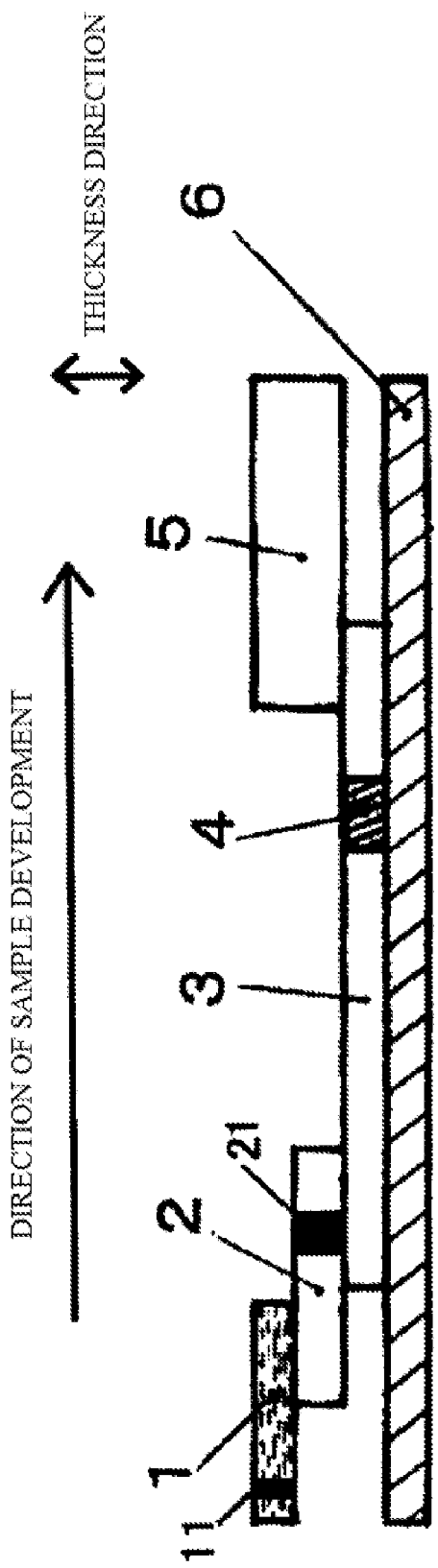
FIG. 1 is a cross section for explaining the structure of the immunochromatographic device of an embodiment of the present invention.

The present invention is explained in detail below.

An embodiment of the present invention is based on an immunochromatographic device, an immunochromatographic kit and an immunochromatographic detection method (sometimes called an immunochromatographic detection system below) which are for detecting a detection target with detection means by extracting a substance to be detected (an antigen) from the detection target in an analyte and developing a complex formed through reaction with a binding substance (an antibody) that specifically binds to the substance to be detected (the antigen) (antigen-antibody reaction) on a chromatography medium.

As the antibody which most specifically reacts with and binds to the antigen, for example, a monoclonal antibody, a polyclonal antibody or another known antibody which specifically binds to the antigen can be used.

By labeling the antibody, the detection target can be detected. As the label, an enzyme, a coloring substance, a fluorescent substance, a radioactive substance or the like can be used. For example, the label may be selected in a manner that the characteristics of the immunochromatographic detection method, namely the simple operation and the short test period, are exhibited, or the label may be selected taking the types of the antibody and the antigen and the like into consideration.

In order that the characteristics of the immunochromatographic detection method, namely the simple operation and the relatively short determination period, can be exhibited, the detection means is characterized by having the property of enabling accurate determination by a visual evaluation. When the time, the accuracy and the like are important, however, various types of detection means such as spectrophotometric detection and radiation detection can be additionally used for the detection.

Any bacterium can be applied as the detection target of the present invention as long as a bacterium-specific antigen polysaccharide is extracted from the bacterium with nitrous acid generated by the immunochromatographic detection system of the present invention. In particular, a detection target containing a Gram-positive bacterium having a thick peptidoglycan layer is preferably used.

Examples include staphylococci, streptococci, pneumococci, bacilli, *Bacillus anthracis, Bacillus cereus, Corynebacterium diphtheriae, Listeria, Clostridium tetani, Clostridium botulinum, Clostridium perfringens* and the like. The present invention is preferably used for staphylococci, streptococci and pneumococci, which are cocci, of these examples. The present invention is most preferably used for streptococci, particularly hemolytic streptococci.

The analyte containing the detection target can be, for example, not only a biological sample such as saliva, nasal discharge, nasal swab, nasal aspirate, sputum, pharyngeal swab, alveolar lavage, rectal swab, fecal suspension, urine and amniotic fluid but also a sample such as food extract, service water, sewage and culture solution, and the analyte is not particularly limited.

In particular, the present invention is useful when the causative bacteria contained in such an analyte include a Gram-positive bacterium, especially a hemolytic *Streptococcus*. In the present invention, the detection target can be a hemolytic *Streptococcus* contained in saliva or the like collected from a patient with a respiratory disease or the like, and the detection target, the hemolytic *Streptococcus*, can be detected by detecting a polysaccharide extracted from the hemolytic *Streptococcus* as a substance to be detected.

Although embodiments of the immunochromatographic device, the immunochromatographic kit and the immunochromatographic detection method of the present invention are explained one by one below, the present invention is not limited to the embodiments shown below.

<Immunochromatographic Device>

The immunochromatographic device of the present invention is an immunochromatographic device for detecting a detection target in an analyte which includes a sample droplet-receiving member, a labeling substance-holding member having a labeling substance-containing part, a chromatography medium member having a detection part and an absorption member and which contains a nitrous acid compound and an organic acid or an organic acid derivative (also together called an organic acid or the like below). In the immunochromatographic device, the sample droplet-receiving member, the labeling substance-holding member, the chromatography medium member and the absorption member are arranged in a manner that a sample develops in this order. The immunochromatographic device has a part containing the nitrous acid compound and a part containing the organic acid or the like at upstream positions from the labeling substance-containing part, and the part containing the nitrous acid compound and the part containing the organic acid or the like are not substantially in contact with each other in the thickness direction.

Because the part containing the nitrous acid compound and the part containing the organic acid or the like are in the arrangement, the organic acid or the like and the nitrous acid compound can be inhibited from diffusing and coming into contact with each other in the device during the storage of the device, which means that the generation of nitrous acid can be inhibited.

It is speculated that the reason why the nitrous acid compound and the organic acid or the like can be inhibited from diffusing and coming into contact with each other in the device during the storage of the device when the part containing the nitrous acid compound and the part containing the organic acid or the like are in the arrangement is that the reaction of the nitrous acid compound and the organic acid or the like is restricted.

The term "member" and the term "part" used in this description have different meanings. For example, the "member containing the nitrous acid compound (the organic acid or the like)" is defined as the entire "member" which contains the nitrous acid compound (the organic acid or the like), while the "part containing the nitrous acid compound (the organic acid or the like)" is defined as the area which actually contains the nitrous acid compound (the organic acid or the like) in the member containing the nitrous acid compound (the organic acid or the like). In this regard, the "part" sometimes refers to the entire member, not just a partial area of the member.

In this description, the member having the part containing the nitrous acid compound is sometimes called a nitrous acid compound-containing member, and the member having the part containing the organic acid or the like is sometimes called an organic acid etc.—containing member.

In this description, the "direction of sample development" means the direction in which the sample develops (moves) before the sample is absorbed by the absorption member after the sample is dropped to the sample droplet-receiving member, and for example, the direction of sample development is the direction of the arrow (rightwards arrow) in the immunochromatographic device shown in FIG. 1. Also, the "upstream" in the present invention means the opposite direction to the "direction of sample development" and means the direction to (side at) the sample droplet-receiving member seen from the absorption member.

The immunochromatographic device of the present invention is explained specifically below referring to the drawings.

As shown in FIG. 1, in an embodiment of the present invention, the immunochromatographic device is composed of members including at least a sample droplet-receiving member (1), a labeling substance-holding member (2) having a labeling substance-containing part, a chromatography medium member (3) having a detection part (4) and an absorption member (5).

In the device, the members constituting the immunochromatographic device are linked and arranged in a manner that the sample develops in the sample droplet-receiving member (1), the labeling substance-holding member (2), the chromatography medium member (3) having the detection part (4) and the absorption member (5) in this order.

Figure 2:
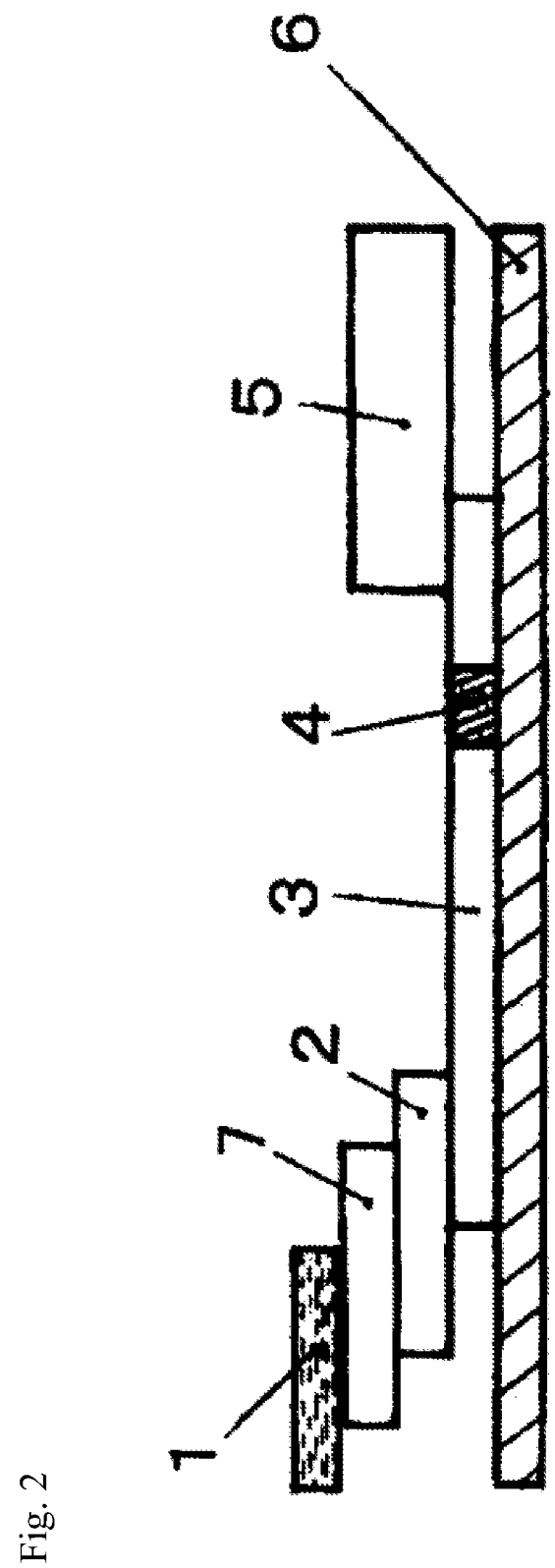
FIG. 2 is a cross section for explaining the structure of the immunochromatographic device of another embodiment of the present invention.

The device may have a member other than the above members at any position, and for example, another member (for example, an organic acid etc.—containing member 7 or the like) may be between the sample droplet-receiving member (1) and the labeling substance-holding member (2) as shown in FIG. 2. Regarding the embodiments in which the members are linked, the members may be linked in a manner that the members overlap each other as shown in FIG. 1, or the members do not overlap each other but are linked in a manner that the sides of the members are in contact with each other in the direction of sample development.

The sample droplet-receiving member (1) means a member having a part to which a sample containing an analyte (also simply called a sample below) is dropped (called a sample droplet-receiving part 11 below) in the immunochromatographic device and is the member indicated with reference number 1 in FIG. 1.

The sample droplet-receiving part 11 refers to a partial area to which the sample is dropped in the sample droplet-receiving member (1). The position of the sample droplet-receiving part 11 in the sample droplet-receiving member (1) is not particularly restricted and may be, for example, at or around an end of the sample droplet-receiving member (1) or in or around the middle of the sample droplet-receiving member (1). The sample droplet-receiving member (1) can contain the nitrous acid compound or the organic acid or the like described below or any other reagent which does not impair the effects of the present invention.

The sample droplet-receiving member (1) can be composed of a porous sheet having the properties of rapidly absorbing the sample but allowing the sample to move rapidly with weak holding power. Examples of the porous sheet include cellulose filter paper, glass fiber filter paper, polyurethane, polyacetate, cellulose acetate, nylon, cotton cloth and the like. Regarding the shape of the sample droplet-receiving member (1), a sheet can be used.

The labeling substance-holding member (2) is a member having a part containing a labeling substance obtained by labeling a reagent component with a labeling component (to be referred as a labeling substance-containing part 21 below) and is the member indicated with reference number 2 in FIG. 1.

The labeling substance-containing part 21 refers to an area which actually contains the labeling substance in the labeling substance-holding member (2). The labeling substance-containing part 21 may occupy a partial area of the labeling substance-holding member (2) as shown in FIG. 1 or occupy the entire area of the labeling substance-holding member (2).

When the labeling substance-containing part 21 occupies a partial area of the labeling substance-holding member (2), the position of the labeling substance-containing part 21 in the labeling substance-holding member (2) is not particularly restricted and may be, for example, at or around an end of the labeling substance-holding member (2) or in or around the middle of the labeling substance-holding member (2). The labeling substance-holding member (2) can contain the nitrous acid compound or the organic acid or the like described below or any other reagent which does not impair the effects of the present invention.

Examples of the labeling component include metal particles, latex particles, an enzyme, a fluorescent compound and the like, and metal particles are preferable of these examples. The reagent component is composed of particles or molecules which are capable of recognizing the analyte and is preferably a monoclonal antibody, a polyclonal antibody or a fragment thereof (a first reagent).

As the metal particles, particles of a single noble metal such as gold, silver, platinum, germanium, rhodium and palladium and composite particles of the noble metals can be preferably used. Of these examples, gold is sensitive to a change in hues and thus is particularly preferable.

The average particle diameter of the metal particles is preferably 1 nm to 500 nm, more preferably 10 nm to 250 nm, further preferably 35 nm to 100 nm. Nano-sized gold particles having such an average particle diameter are called gold nanoparticles.

In the immunochromatographic detection method, taking the particle diameter of gold, its particle size distribution, its color and the like into consideration, gold composite particles in which platinum particles are supported on the surface of gold particles can be used as a label for the immunochromatographic detection method or used to improve the utility as a dye agent for proteins. When a so-called sensitizer such as a gold label-sensitizing agent having a functional group which can bind to the surface of the metal particles and a reactive group which can bind to the antibody is used, the measurement sensitivity can be enhanced.

For the labeling substance-holding member (2), for example, a membrane of glass fibers or cellulose or the like is usually used. Regarding the shape of the labeling substance-holding member (2), a sheet can be used.

The immunochromatographic device of the present invention has the part containing the nitrous acid compound and the part containing the organic acid or the like at upstream positions from the labeling substance-containing part 21. Because the immunochromatographic device of the present invention has such a structure, the nitrous acid compound and the organic acid or the like react with each other and generate nitrous acid at an upstream position from the labeling substance-containing part 21, and the substance to be detected can be extracted from the detection target. Thus, the detection target can move to the labeling substance-containing part 21 in the state in which the substance to be detected is extracted, and the substance to be detected (for example, a polysaccharide) can be labeled.

The part containing the nitrous acid compound and the part containing the organic acid or the like may be in a same member or in different members. An embodiment in which the part containing the nitrous acid compound and the part containing the organic acid or the like are in different members means an embodiment in which one of the nitrous acid compound and the organic acid or the like is contained at an upstream position from the labeling substance-containing part 21 and in which a member at an upstream position from the member containing the one contains the other one of the nitrous acid compound and the organic acid or the like.

When the part containing the nitrous acid compound and the part containing the organic acid or the like are in a same member, the part containing the nitrous acid compound and the part containing the organic acid or the like are of course not at a same position. This is because the reaction of the nitrous acid compound and the organic acid or the like advances during the storage of the device.

The members which may have the part containing the nitrous acid compound and/or the part containing the organic acid or the like are not limited to the two members of the sample droplet-receiving member (1) and the labeling substance-holding member (2) only. When there is another member between the sample droplet-receiving member (1) and the labeling substance-holding member (2), the member can contain the nitrous acid compound or the organic acid or the like. The number of such members may be one or more.

For example, as shown in FIG. 2, the organic acid etc.—containing member 7 can be possessed between the sample droplet-receiving member (1) and the labeling substance-holding member (2).

In the immunochromatographic device of the present invention, the part containing the nitrous acid compound may be positioned at an upstream position from the part containing the organic acid or the like in the direction of sample development or positioned at a downstream position from the part containing the organic acid or the like in the direction of sample development, as long as the part containing the nitrous acid compound is at an upstream position from the labeling substance-containing part. However, the part containing the nitrous acid compound and the part containing the organic acid or the like are not at a same position as described above.

When the part containing the nitrous acid compound is positioned at an upstream position from the part containing the organic acid or the like in the direction of sample development, the nitrous acid compound moves to the part containing the organic acid or the like in the device, and the two come into contact/react with each other and generate nitrous acid. When the part containing the nitrous acid compound is positioned at a downstream position from the part containing the organic acid or the like in the direction of sample development, the organic acid or the like moves to the part containing the nitrous acid compound in the device, and the two come into contact/react with each other and generate nitrous acid.

In particular, the part containing the nitrous acid compound is preferably at any position in the sample droplet-receiving member (1), and the part containing the organic acid or the like is preferably at any position in the organic acid etc.—containing member 7.

The shortest physical distance between the downstream one of the part containing the nitrous acid compound and the part containing the organic acid or the like and the labeling substance-containing part 21 in the labeling substance-holding member (2) is preferably from 20 mm to 40 mm. This is because a distance of less than 20 mm decreases the extraction efficiency and decreases the sensitivity while a distance exceeding 40 mm prolongs the detection period.

The present invention is characterized by having a structure in which the part containing the nitrous acid compound and the part containing the organic acid or the like are not substantially in contact with each other in the thickness direction. Due to this structure, the nitrous acid compound and the organic acid or the like can be inhibited from coming into contact with each other in the device during the storage of the device, which means that the generation of nitrous acid during the storage of the device can be inhibited. Thus, the storage stability of the device can be improved.

Here, the "thickness direction" means the direction of the thicknesses of the sample droplet-receiving member, the labeling substance-holding member, the chromatography medium member, the absorption member and the like described above in the immunochromatographic device of the present invention. When the members are sheets, the thickness direction refers to the thickness direction of the sheets. For example, in the immunochromatographic device shown in FIG. 1, the thickness direction is the direction of the arrow (up down arrow).

When the members are layered and arranged, the "thickness direction" means the "direction of layering of the members", namely the direction in which the members are layered. In other words, the "thickness direction" means the direction perpendicular to the direction of sample development.

The "contact" means the physical contact between the part containing the nitrous acid compound and the part containing the organic acid or the like.

That "the part containing the nitrous acid compound and the part containing the organic acid or the like are not substantially in contact with each other in the thickness direction" means that the length in the direction of sample development of the area of the contact between the part containing the nitrous acid compound and the part containing the organic acid or the like in the thickness direction (also called the length of the overlap below) is 0.5 mm or less.

In the present invention, the length in the direction of sample development of the area of the contact in the thickness direction is preferably 0.3 mm or less, more preferably 0.1 mm or less, further preferably 0 mm. That the length in the direction of sample development of the area of the contact in the thickness direction is 0 mm means that the part containing the nitrous acid compound and the part containing the organic acid or the like are not in contact with each other at all in the thickness direction.

When the length in the direction of sample development of the area of the contact in the thickness direction is 0.5 mm or less, the organic acid or the like and the nitrous acid compound can be prevented from diffusing in the device and coming into contact with each other during the storage of the device.

Although the structure in which the part containing the nitrous acid compound and the part containing the organic acid or the like are not substantially in contact with each other in the thickness direction is explained below with specific examples, the embodiments of the present invention are not restricted to the examples below.

Figure 3A:
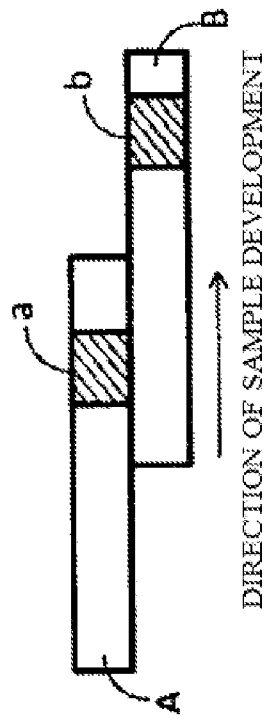
Figure 3B:
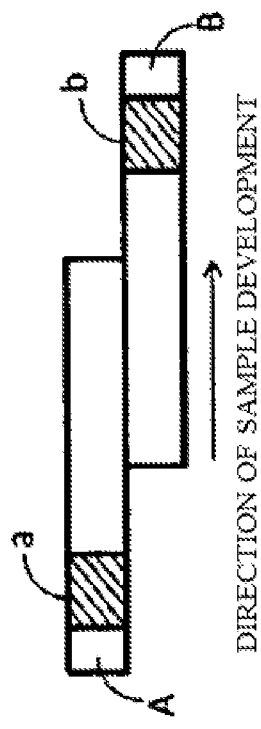
Figure 3C:
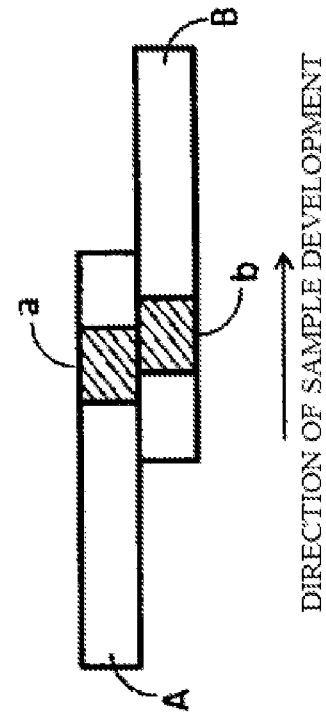

FIG. 3A, FIG. 3B and FIG. 3C show specific examples showing the structures of embodiments of the present invention, in which the part containing the nitrous acid compound and the part containing the organic acid or the like are not substantially in contact with each other in the thickness direction.

The embodiments shown in FIG. 3A and FIG. 3B are embodiments in which the part a containing the nitrous acid compound and the part b containing the organic acid or the like are not in contact with each other in the thickness direction although the "member A" including the part containing the nitrous acid compound and the "member B" including the part containing the organic acid or the like are in contact with each other and overlap in the thickness direction.

The embodiment shown in FIG. 3C is an embodiment in which the "member A" including the part containing the nitrous acid compound and the "member B" including the part containing the organic acid or the like are layered with a "member C" in-between. This is an embodiment in which the "member A" and the "member B" do not overlap in the state of being in contact with each other in the thickness direction and in which the part a containing the nitrous acid compound and the part b containing the organic acid or the like are not in contact with each other in the thickness direction. The member C should not prevent the sample development and is preferably composed of a porous sheet having the property of allowing the sample to move rapidly.

Figure 3D:
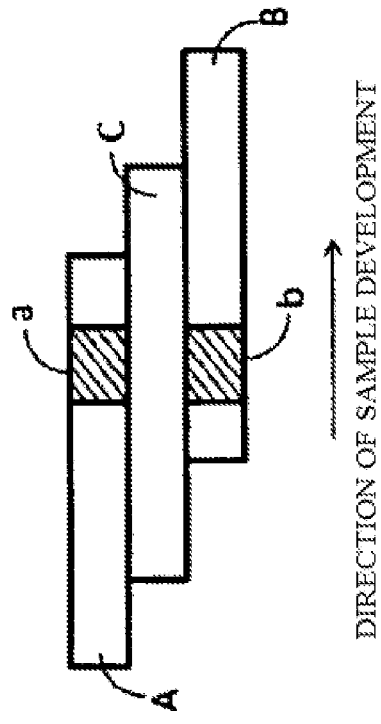

On the contrary, the structure shown in FIG. 3D is a structure in which the "member A" including the part containing the nitrous acid compound and the "member B" including the part containing the organic acid or the like overlap in the state of being in contact with each other in the thickness direction and in which the part a containing the nitrous acid compound and the part b containing the organic acid or the like are in contact with each other in the thickness direction.

Because the structure of FIG. 3D is a structure in which the part containing the nitrous acid compound and the part containing the organic acid or the like are substantially in contact with each other in the thickness direction and thus is different from the structures of the embodiments of the present invention.

Figure 4A:
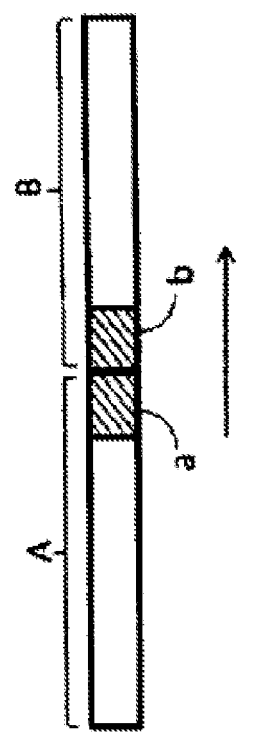
FIG. 4A and FIG. 4B are cross sections for explaining partial structures of the immunochromatographic devices of other embodiments of the present invention.
Figure 4B:
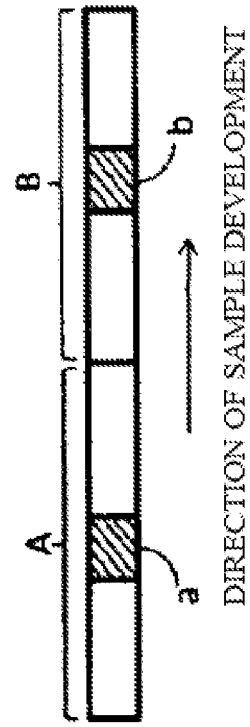

FIG. 4A and FIG. 4B show specific examples showing the structures of embodiments of the present invention, in which the part containing the nitrous acid compound and the part containing the organic acid or the like are not substantially in contact with each other in the thickness direction.

The embodiments shown in FIG. 4A and FIG. 4B are embodiments in which the "member A" including the part containing the nitrous acid compound and the "member B" including the part containing the organic acid or the like do not overlap in the thickness direction but in which the "member A" and the "member B" are in contact with each other in the direction of sample development. In the embodiments, the part a containing the nitrous acid compound and the part b containing the organic acid or the like are not in contact with each other in the thickness direction. In FIG. 4B, the part a containing the nitrous acid compound and the part b containing the organic acid or the like are in contact with each other in the direction of sample development but are not in contact with each other in the thickness direction.

The nitrous acid compound in the present invention is not particularly restricted as long as the nitrous acid compound generates nitrous acid by reacting with an acid and does not adversely affect the test. The nitrous acid compound is preferably a nitrite. Examples of the nitrite include inorganic nitrites such as sodium nitrite, potassium nitrite, calcium nitrite and magnesium nitrite and organic nitrous acid compounds such as methyl nitrite, ethyl nitrite, butyl nitrite and amyl nitrite. A mixture thereof may also be used. The nitrous acid compound is preferably an inorganic nitrite, especially preferably an alkali metal salt of nitrous acid, most preferably sodium nitrite.

The amount of the nitrous acid compound in the immunochromatographic device of the present invention is preferably from 50 mmol to 200 mmol/device, more preferably from 75 mmol to 175 mmol/device.

The organic acid or the organic acid derivative of the present invention is not particularly restricted as long as the organic acid or the organic acid derivative generates nitrous acid by reacting with the nitrous acid compound and does not denature/precipitate the proteins and the like in the device of the present invention.

Examples of the organic acid include organic sulfonic acids, organic carboxylic acids, organic phosphoric acids and the like. Specific examples include acetic acid, tartaric acid, itaconic acid, oxalic acid, succinic acid, citric acid, phthalic acid, glycolic acid, chloroacetic acid, fluoroacetic acid, benzoic acid, benzenesulfonic acid and the like. The organic acid may also be a fixed acid such as polysulfonic acids, polycarboxylic acids, polystyrene and polyacrylic acids and is not limited.

The organic acid derivative may be an imide of an organic acid, an amide of an organic acid, an ester of an organic acid, an organic acid anhydride or the like.

The organic acid or the organic acid derivative is not limited to a low molecular weight compound only, and an oligomer or a polymer can also be used. Two or more kinds may be contained.

Of the examples, in view of the storage stability of the immunochromatographic device or the pH described below, a nitrogen-containing heterocyclic compound having a carbonyl group is preferable, and a nitrogen-containing heterocyclic compound represented by the following formula (1) is further preferable.

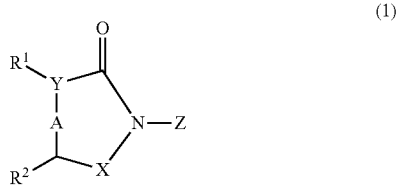

(1)

In the formula (1), $R^1$ and $R^2$ each independently represents a hydrogen atom, a carbonyl group or an alkyl group which may have a substituent, and alkyl groups may bind to each other to form a ring and form an alicyclic hydrocarbon ring or an aromatic hydrocarbon ring.

A represents a single bond or a double bond, and X represents —C(=O)— or —(CH$_2$)$_n$—. Y represents a carbon atom or a nitrogen atom, and n is 1 or 2.

Z represents a hydrogen atom, a hydroxyl group, an alkyl group which may have a substituent, —C(=O)R$^3$ or —O—C(=O)R$^3$. R$^3$ represents an alkyl group which may have a substituent or an alkoxy group.

The compound represented by the formula (1) of the present invention is specifically phthalimide, N-acetylphthalimide, N-(tert-butoxycarbonyloxy)phthalimide, N-hydroxysuccinimide, N-acetoxysuccinimide, N-carbobenzoxyoxysuccinimide, di(N-succinimidyl) carbonate, hydantoin or the like.

Of these compounds, at least one selected from the group consisting of phthalimide, N-acetylphthalimide, N-(tert-butoxycarbonyloxy)phthalimide, N-hydroxysuccinimide, N-acetoxysuccinimide and hydantoin is preferable.

N-Acetoxysuccinimide and hydantoin are more preferable, and N-acetoxysuccinimide is particularly preferable.

A mixture thereof can be used as the organic acid and/or the organic acid derivative.

It is preferable to use the nitrogen-containing heterocyclic compound represented by the formula (1) because a broad pH range can be set during the generation of nitrous acid. That is, when citric acid is used as the organic acid, for example, the pH range during the reaction of the organic acid and the nitrous acid compound is restricted to around 6.8 to 7.0. When the nitrogen-containing heterocyclic compound represented by the formula (1) is used, however, a broad pH range of around 6.5 to 8.0 can be set. As a result, for example, even when the pH of the development solution changes due to a component of the analyte, nitrous acid can be generated efficiently.

The amount of the organic acid or the like in the immunochromatographic device of the present invention is preferably from 10 mmol to 40 mmol/device, more preferably from 20 mmol to 30 mmol/device. When the amount is in the range, nitrous acid can be generated efficiently.

The chromatography medium member (3) is obtained by forming the detection part (4) on a membrane support. The membrane support is not particularly limited as long as the membrane support can absorb and move the sample through a capillary phenomenon.

The chromatography medium member (3) for use can be selected, for example, from the group consisting of nitrocellulose, cellulose acetate, nylon, polyether sulfones, polyvinyl alcohol, polyesters, glass fibers, polyolefins, cellulose and artificial polymers of mixed fibers thereof. Regarding the shape of the chromatography medium member (3), a sheet can be used.

In the detection part (4), a monoclonal antibody, a polyclonal antibody or a fragment thereof (a second reagent) is supported and immobilized on a nitrocellulose sheet.

Filter paper composed of glass fibers, cellulose fibers or the like, which is a material capable of rapidly absorbing the excess sample, is generally used for the absorption member (5), but a material which is further capable of holding the absorbed liquid to prevent the backflow is more preferably used (JP-A-2012-189346). Regarding the shape of the absorption member (5), a sheet can be used.

Moreover, as described above, members other than those described above may be at any positions of the device of the present invention. The members can be each composed of a porous sheet having the properties of rapidly absorbing the sample but allowing the analyte (analyte sample) to move rapidly with weak holding power.

Examples of the porous sheet include cellulose filter paper, glass fiber filter paper, polyurethane, polyacetate, cellulose acetate, nylon, cotton cloth and the like. Regarding the shapes of the members, sheets can be used.

The immunochromatographic device of the present invention can include a backing sheet (6). The backing sheet (6) is a base material. One surface of the backing sheet (6) is adhesive because an adhesive is applied on the surface or an adhesive tape is attached. The sample droplet-receiving member (1), the labeling substance-holding member (2), the chromatography medium member (3) having the detection part (4) and the absorption member (5) are partially or entirely closely adhered and provided on the adhesive surface.

The same applies also when the immunochromatographic device of the present invention includes a member other than the members described above (for example, the nitrous acid compound-containing member, the organic acid etc.—containing member or the like). The base material is not particularly limited as long as the backing sheet (6) is not permeable or is moisture impermeable with respect to the sample solution due to the adhesive.

One or both of the reagent component used for the detection part (4) (the second reagent) and the reagent component used for the labeling reagent (the first reagent) may be a monoclonal antibody or a polyclonal antibody. It is preferable that the reagent component used for the detection part (4) (the second reagent) is a polyclonal antibody and that the reagent component used for the labeling reagent (the first reagent) is a monoclonal antibody.

The monoclonal antibodies, the polyclonal antibodies and the fragments thereof are known and available and can be prepared by known methods. Examples of the kinds of animal producing the antibodies include human, mouse, rat, rabbit, goat, horse and the like. The immunoglobulin may be any of IgG, IgM, IgA, IgE and IgD.

In particular, it is preferable to use a rabbit-derived antibody for both of the reagent component used for the labeling substance-holding member (2) (the first reagent) and the reagent component used for the detection part (4) (the second reagent).

The immunochromatographic device of the present invention is usually subjected to drying treatment before being completed as a product. The drying temperature is, for example, 20° C. to 50° C., and the drying time is 0.5 hours to one hour.

<Immunochromatographic Kit>

The immunochromatographic kit of the present invention includes the immunochromatographic device and an analyte dilution solution for diluting an analyte.

In the immunochromatographic kit of the present invention, the analyte dilution solution can be used also as a development solution. When the analyte dilution solution is used as a development solution, an analyte-containing solution obtained by previously mixing the analyte and the analyte dilution solution (development solution) can be supplied/dropped as a sample to the sample droplet-receiving member for development. Alternatively, the analyte dilution solution (development solution) may be supplied and dropped to the sample droplet-receiving member for development after supplying and dropping the analyte to the sample droplet-receiving member in advance.

In general, when the pH condition of the development solution is an acidic condition, the efficiency of generation of nitrous acid generated through reaction of the nitrous acid compound and the organic acid or the like is high, and the extraction efficiency of the antigen can be improved. An acidic pH condition, however, may cause problems, such as the precipitation of proteins including for example casein or salts thereof contained in the immunochromatographic device or in the analyte dilution solution described below, highly viscous proteins contained in the analyte and the like, and improper development due to the agglutination of the labeling substance.

Accordingly, the pH condition of the development solution in the present invention is preferably pH at which nitrous acid is generated and pH at which the proteins such as casein, the highly viscous proteins contained in the analyte and the like do not precipitate and at which the agglutination of the labeling substance is not caused. As the pH condition, pH is from 6.5 to 8.5, preferably from 6.6 to 8.0, and most preferably from 6.8 to 7.5.

At the pH, the precipitation of the proteins or the agglutination of the labeling substance is not easily caused. As described above, the organic acid or the organic acid derivative represented by the formula (1) is preferably used as the organic acid or the organic acid derivative in order to efficiently generate nitrous acid in the pH range.

In the immunochromatographic kit of the present invention, the analyte dilution solution and the parts of the immunochromatographic device can contain reagents such as a surfactant including a nonionic surfactant or the like, a salt, a buffer and an additive in addition to the reagents described above within the scope which does not impair the effects of the present invention.

Examples of the nonionic surfactant which can be used for the immunochromatographic kit of the present invention include polyoxyethylene alkyl ethers, polyoxyethylene/polyoxypropylene alkyl ethers, polyoxyethylene sorbitan fatty acid esters (product name "Tween" series), polyoxyethylene p-t-octylphenyl ether (product name "Triton" series), polyoxyethylene p-t-nonylphenyl ether (product name "Triton N" series), alkyl polyglucosides, fatty acid diethanol amides, alkyl monoglyceryl ethers and the like. An ionic surfactant other than the nonionic surfactant or the like can also be added and used within the scope which does not cause any adverse effects.

The amount of the nonionic surfactant used for the analyte dilution solution or the immunochromatographic device of the present invention is preferably in the range of 0.2 mass % to 2.0 mass %, and the nonionic surfactant can be more preferably contained in an amount in the range of 0.5 mass % to 1.5 mass %.

An amount of less than 0.2 mass % has a tendency towards instable development, making it impossible to make accurate determination, or has a tendency towards somewhat difficulty in accurate determination because nonspecific reaction cannot be inhibited. A concentration exceeding 2.0 mass % is higher than needed and does not affect preferably on the inhibition of nonspecific reaction. Moreover, such an amount has no technical meanings; is not economical; and is a waste.

Typical examples of the salt used for the analyte dilution solution or the immunochromatographic device of the present invention include sodium chloride, potassium chloride, calcium chloride, magnesium chloride and the like. Sodium chloride is preferable.

The concentration of the salt used for the analyte dilution solution or the immunochromatographic device of the present invention is preferably in the range of from 1 mM to 500 mM, more preferably in the range of from 5 mM to 200 mM, and further preferably in the range of from 10 mM to 50 mM. When the concentration is lower than 1 mM, for example as low as 0.1 mM, the effect of extracting a protein becomes insufficient. An amount exceeding 500 mM, for example as high as 1 M or 2 M, has no technical meanings. Such a concentration is higher than needed; is not economical; and is a waste.

Not only one kind but also two or more kinds can be added and used as the salt used for the analyte dilution solution or the immunochromatographic device of the present invention.

The buffer used for the analyte dilution solution or the immunochromatographic device of the present invention is not particularly restricted as long as the buffer has the effect of causing no fatal effect even when the concentration changes due to addition of the sample or evaporation or dilution of the sample or when small amounts of foreign substances contaminate from the outside (buffering effect).

In the present invention, examples of the buffer include phosphate buffer (phosphoric acid+sodium phosphate), acetate buffer (acetic acid+sodium acetate), citrate buffer (citric acid+sodium citrate), borate buffer, tris-hydrochloric acid buffer (tris(hydroxylmethyl)aminomethane+hydrochloric acid), TE buffer (tris+ethylenediaminetetraacetic acid), TAE buffer (tris+acetic acid+ethylenediaminetetraacetic acid), TBE buffer (tris+boric acid+ethylenediaminetetraacetic acid), HEPES buffer (2-[4-(2-hydroxyethyl)-1-piperazinyl] ethanesulfonic acid), Bicine buffer (N,N-bis(2-hydroxyethyl)glycine buffer) and the like.

The buffer is preferably phosphate buffer, tris-hydrochloric acid buffer, acetate buffer or the like, more preferably tris-hydrochloric acid buffer. In the immunochromatographic detection system of the present invention, two or more kinds of buffer can be used, without any restriction, within the scope that does not cause any adverse effects.

The concentration of the buffer used in the present invention is preferably in the range of from 10 mM to 500 mM, more preferably in the range of from 10 mM to 300 mM, further preferably in the range of from 30 mM to 100 mM.

When the concentration is lower than 10 mM, the buffering effect becomes insufficient, and the precipitation of the protein components and the agglutination of the labeling particles are not inhibited sufficiently. A concentration exceeding 500 mM is higher than needed, is not economical and is a waste.

The optimum pH range of the buffer is 7.1 to 9.8.

In the analyte dilution solution or the immunochromatographic device of the present invention, it is also possible and effective to add and use, without any restriction, a kind or two or more kinds of additives which are known to inhibit side reaction based on biological affinity or inhibit nonspecific reaction, such as proteins (for example, bovine serum albumin, gelatin, casein and the like), polymer compounds (for example, polyethylene glycol, methyl cellulose, polyvinylpyrrolidone, polyvinyl alcohol, dextran and the like), ionic surfactants or polyanions (for example, dextran sulfate, heparin, polystyrene sulfonate, chondroitin sulfate and the like), which are for promoting antigen-antibody reaction or inhibiting nonspecific reaction, antibacterial agents and the like.

It is also possible and effective that, without any restriction, a kind or two or more kinds of the proteins, the polymer compounds, the ionic surfactants or the polyanions, which are for promoting antigen-antibody reaction or inhibiting nonspecific reaction, the antibacterial agents and the like are held on the path of the mobile phase on the chromatography medium member constituting the stationary phase.

The concentrations of the additives contained in the analyte dilution solution or the immunochromatographic device of the present invention are preferably in the range of from 0.01 mass % to 20 mass %, more preferably in the range of from 0.1 mass % to 10 mass %, and further preferably in the range of from 0.5 mass % to 5 mass %. When the concentrations are lower than 0.01 mass %, nonspecific reaction cannot be inhibited, and accurate determination cannot be made. A concentration exceeding 20 mass % is higher than needed, is not economical and is a waste.

Water is usually used as a solvent of the analyte dilution solution. Moreover, in addition to the nonionic surfactant, the salt, the buffer and the like, a kind or two or more kinds of the following materials may be added to the solvent: a protein, a polymer compound (such as PVP), an ionic surfactant or a polyanion for promoting antigen-antibody reaction or inhibiting nonspecific reaction; an antibacterial agent; a chelating agent; and the like.

The order of addition is not particularly restricted, and simultaneous addition is also acceptable. An analyte-containing solution obtained by previously mixing the analyte to be detected and the analyte dilution solution can be supplied and dropped to the sample droplet-receiving member for development, or the analyte dilution solution may be supplied/dropped to the sample droplet-receiving member for development after supplying and dropping the analyte to the sample droplet-receiving member in advance.

When the immunochromatographic device contains any reagent, the reagent is applied to the part which should contain the reagent and then dried, or the part is impregnated with the reagent and then dried, as an example method. By such a method, an embodiment in which the reagent is supported or held in the part can be achieved.

When the reagent is contained in a part of a member as a spot, not in the entire member, for example, a method of masking the member and then spraying the reagent or the like may be used.

The principles of the determination in a typical kit structure of the present invention are explained in 1 to 64 below.

1. A certain amount (usually 0.1 ml to 2 ml) of an analyte-containing solution obtained by diluting an analyte with the analyte dilution solution is dropped as a sample to the sample droplet-receiving member (1) (the sample droplet-receiving part 11) of the immunochromatographic device. When the analyte-containing solution is dropped, the analyte-containing solution is rapidly absorbed by the sample droplet-receiving member (1) and immediately starts to move to the labeling substance-holding member (2).

2. The nitrous acid compound, which is held at any upstream position from the labeling substance-containing part 21 in the direction of sample development, dissolves in the water content of the analyte-containing solution which has moved to the position and moves with the analyte.

3. Next, the analyte-containing solution containing the nitrous acid compound dissolved therein comes into contact with the organic acid or the like, which is held at any upstream position from the labeling substance-containing part 21 in the direction of sample development, and the nitrous acid compound and the organic acid or the like react with each other and generate nitrous acid. When the detection target, such as a hemolytic *Streptococcus* or the like, is contained in the analyte for example, nitrous acid extracts a polysaccharide (the substance to be detected) on the surface of the bacterium.

4. Next, the analyte-containing solution containing nitrous acid moves to the labeling substance-containing part 21. When the analyte-containing solution passes through the labeling substance-containing part 21, the labeling reagent (the first reagent) held in the labeling substance-containing part 21 dissolves in the water content of the analyte-containing solution; labels the substance to be detected (for example, a polysaccharide or the like); and moves with the analyte.

5. Next, the labeling reagent dissolved in the water content of the analyte-containing solution passes through the detection part (4) on the chromatography medium member (3). Here, when the substance to be detected (for example, a polysaccharide) is contained in the analyte-containing solution, the substance to be detected is immobilized in the detection part due to specific antigen-antibody binding reaction in a manner that the substance to be detected is sandwiched between the antibody (the second reagent) supported and immobilized in the detection part (4) and the labeling reagent (the first reagent), and the detection part (4) is colored. In this manner, the detection target can be detected. When the substance to be detected (for example, a polysaccharide) is not contained in the analyte, the specific binding reaction does not occur even when the labeling reagent (the first reagent) dissolved in the water content of the analyte-containing solution passes through the detection part (4) on the chromatography medium member (3), and thus the detection part (4) is not colored.

6. At the end, the analyte-containing solution moves to the absorption member (5) and is absorbed.

In this manner, the presence or absence of the substance to be detected (for example, a polysaccharide) in the analyte can be accurately determined.

<Immunochromatographic Detection Method>

The immunochromatographic detection method of the present invention includes the following steps (i) to (v) and detects a detection target in an analyte using the immunochromatographic kit.

(i) A step of dropping an analyte-containing solution obtained by diluting the analyte with the analyte dilution solution to the sample droplet-receiving member.

(ii) A step of extracting a substance to be detected from the detection target in the analyte with nitrous acid generated through reaction of the nitrous acid compound and the organic acid or the organic acid derivative.

(iii) A step of labeling the substance to be detected in the labeling substance-holding member.

(iv) A step of allowing the analyte-containing solution to move on the chromatography medium member and detecting the detection target in the detection part.

(v) A step of absorbing the analyte-containing solution with the absorption member.

The details of the steps are the same as the contents described above for the principles of the determination.

EXAMPLES

Although the effectiveness of the present invention is explained below referring to Examples, the present invention is not limited to the Examples Test Example 1

In this test, it was examined by an accelerated stability test whether or not the storage stability of the immunochromatographic device of the present invention would improve when the part containing the nitrous acid compound and the part containing the organic acid or the like were in specific arrangement.

Example 1

<Production of Immunochromatographic Kit>

In this Example, an immunochromatographic kit composed of an analyte dilution solution, a sample droplet-receiving member (1) containing sodium nitrite, an organic acid etc.—containing member (7) containing phthalimide, a labeling substance-holding member (2), a chromatography medium member (3) having a detection part (4) and an absorption member (5) was produced.

(1) Formation of Detection Part (4) on Chromatography Medium Member (3)

A sheet composed of nitrocellulose (manufactured by Millipore Corporation, product name: HF120, 250 mm×25 mm) was used as a membrane. A rabbit-derived anti-hemolytic *Streptococcus* polyclonal antibody (the second reagent) (manufactured by Meridian Inc.) was diluted to a concentration of 1.0 mg/ml with a 10 mM phosphate buffer (pH 7.4) containing 5 mass % isopropanol, and 150 µL of the diluted solution was applied with a width of 1 mm onto the membrane using an antibody applicator (manufactured by BioDot), dried at 50° C. for 30 minutes and dried at room temperature overnight. The detection part (4) was thus formed on the chromatography medium member (3).

(2) Production of Labeling Substance Solution

To 0.5 mL of a colloidal gold suspension (manufactured by Tanaka Kikinzoku Kogyo K.K.: average particle diameter of 40 nm), 0.1 mL of a rabbit-derived anti-hemolytic *Streptococcus* monoclonal antibody (the first reagent) (manufactured by Virostat Inc.) which had been diluted to a concentration of 0.1 mg/ml with a phosphate buffer (pH 7.4) was added, and the mixture was left to stand still at room temperature for 10 minutes. Then, 0.1 ml of a phosphate buffer (pH 7.4) containing 10 mass % bovine serum albumin was added. After stirring thoroughly, the mixture was centrifuged at 8000×g for 15 minutes, and the supernatant was removed. Then, 0.1 mL of a phosphate buffer (pH 7.4) containing 1 mass % bovine serum albumin was added. A labeling substance solution was thus produced.

(3) Production of Sample Droplet-Receiving Member (1) Containing Sodium Nitrite

An aqueous solution containing 4 mol sodium nitrite in an amount of 0.6 mL was applied to the entire pad of a glass fiber conjugate pad of 12×100 mm (manufactured by Merck KGaA) and freeze-dried, and the sample droplet-receiving member (1) was thus produced.

(4) Production of Organic Acid etc.—Containing Member (7) Containing Phthalimide An aqueous solution containing 1 mol phthalimide in an amount of 0.6 mL was applied to the entire pad of a glass fiber conjugate pad of 12×100 mm (manufactured by Merck KGaA) and freeze-dried, and the organic acid etc.—containing member (7) containing phthalimide was thus produced.

(5) Production of Immunochromatographic Test Strips

A solution obtained by adding 100 µl of a 25 mass % aqueous trehalose solution and 80 µl of a phosphate buffer (pH 9.0) containing 5 mass % casein (final concentration of 1 mass %) to 200 µl of the labeling substance solution produced above was evenly applied to a glass fiber pad of 12×100 mm (manufactured by Millipore Corporation) and then dried with a vacuum dryer, and the labeling substance-holding member (2) was thus produced.

Next, the sample droplet-receiving member (1), the organic acid etc.—containing member (7), the labeling substance-holding member (2), the chromatography medium member (3) having the detection part (4) and the absorption member (5) were pasted to a base material composed of a backing sheet in a manner that the members were linked in this order along the direction of sample development (the order shown in FIG. 2).

The length in the direction of sample development of the area in which the sample droplet-receiving member (1) and the organic acid etc.—containing member (7) were in contact with each other in the thickness direction of the members was adjusted to 0 mm. This means that the members were linked in a manner that the sample droplet-receiving member (1) and the organic acid etc.—containing member (7) were in contact with each other in the direction of sample development. Then, the obtained product was cut with a width of 5 mm with a cutter, and immunochromatographic test strips were thus obtained.

Table 1 below shows the length in the direction of sample development of the area in which the sample droplet-receiving member (1) and the organic acid etc.—containing member (7) were in contact with each other in the thickness direction (the length of the overlap).

(6) Production of Analyte Dilution Solution

An analyte dilution solution which contained a 20 mM tris buffer (pH 8.0) containing 0.5 mass % Tween 20, 0.6 mass % polyvinylpyrrolidone (average molecular weight of 360,000), 1 mass % bovine serum albumin and 150 mM sodium chloride and which was for diluting an analyte and dropping the analyte to an immunochromatographic test strip for development was obtained.

<Measurement (Accelerated Stability Test)>

Using the immunochromatographic test strips and the analyte dilution solution produced above, the presence or absence of a hemolytic *Streptococcus* as the detection target in analytes was examined by the following accelerated stability test, and the storage stability of the immunochromatographic test strips was evaluated.

The immunochromatographic test strips produced above were incubated at 50° C. for 0 hour (without incubation) or for two weeks, and then measurement was conducted using a sample obtained by adding inactivated Group A β-hemolytic *Streptococcus* at 2×10$^6$ org/mL as a positive analyte sample.

The analyte sample in an amount of 150 μL was dropped to the sample droplet-receiving parts of the immunochromatographic test strips and developed, and a visual evaluation was made after 15 minutes. Any of the following marks was given: "+" when the red test line could be visually observed; "++" when the red line could be visually observed clearly; "±" when a light red line could be visually observed; and "−" when the red line could not be visually observed. The results of the evaluation using the positive analyte sample are shown in Table 2.

Measurement was also conducted using the analyte dilution solution which did not contain the hemolytic *Streptococcus* as a negative analyte sample. The results of the evaluation using the negative analyte sample are shown in Table 3.

Comparative Examples 1 and 2

Immunochromatographic kits were produced and measurement was conducted in the same manners as in Example 1 except that the conditions for the production of the immunochromatographic test strips (the length of the overlap between the sample droplet-receiving member (1) and the organic acid etc.—containing member (7)) were changed to the conditions shown in Table 1. The results are shown in Table 2.

In this regard, sodium nitrite was applied to the entire pad of the sample droplet-receiving member (1), and phthalimide was applied to the entire pad of the organic acid etc.—containing member (7). Thus, the length of the overlap between the pad (member) of the sample droplet-receiving member (1) and the pad (member) of the organic acid etc.—containing member (7) the sample droplet receiving member (1) substantially corresponds to the length of the overlap between the part containing sodium nitrite and the part containing phthalimide.

TABLE 1

| Structure | Length of Overlap Between Sample Droplet-Receiving Member (1) and Organic Acid etc.-Containing Member (7) (mm) |
|---|---|
| Example 1 | 0 |
| Comparative Example 1 | 1 |
| Comparative Example 2 | 2 |

TABLE 2

| Incubation Period | 0 hour | 2 weeks |
|---|---|---|
| Example 1 | ++ | ± |
| Comparative Example 1 | ++ | − |
| Comparative Example 2 | ++ | − |

TABLE 3

| Incubation Period | 0 hour | 2 weeks |
|---|---|---|
| Example 1 | − | − |
| Comparative Example 1 | − | − |
| Comparative Example 2 | − | − |

In Example 1, since the sample droplet-receiving member (1) and the organic acid etc.—containing member (7) were not substantially in contact with each other in the thickness direction of the members, the positive analyte could be detected even after two weeks of incubation at 50° C., and it was found that the storage stability was high.

In Comparative Examples 1 and 2, however, since the sample droplet-receiving member (1) and the organic acid etc.—containing member (7) were substantially in contact with each other in the thickness direction of the members (the lengths of the overlaps exceeded 0.5 mm), the positive analyte could not be detected after two weeks of incubation at 50° C., and it was found that the storage stability was not sufficient.

Test Example 2

In this test, the kind of the organic acid or the organic acid derivative in the immunochromatographic device of the present invention was changed, and an accelerated stability test was conducted in a similar manner as in Test Example 1. The accelerated stability test was conducted with incubation at 50° C. for 0 hour (without incubation), for two weeks or for four weeks.

Example 2

Immunochromatographic test strips were produced in the same manner as in Example 1 except that 0.6 mL of an aqueous solution containing N-acetylphthalimide was applied instead of the aqueous solution containing phthalimide to the entire pad of the organic acid etc.—containing member (7), and the accelerated stability test was conducted. The results are shown in Table 4.

Example 3

Immunochromatographic test strips were produced in the same manner as in Example 1 except that 0.6 mL of an aqueous solution containing N-(tert-butoxycarbonyloxy)phthalimide was applied instead of the aqueous solution containing phthalimide to the entire pad of the organic acid etc.—containing member (7), and the accelerated stability test was conducted. The results are shown in Table 4.

Example 4

Immunochromatographic test strips were produced in the same manner as in Example 1 except that 0.6 mL of an aqueous solution containing N-hydroxysuccinimide was applied instead of the aqueous solution containing phthalimide to the entire pad of the organic acid etc.—containing member (7), and the accelerated stability test was conducted. The results are shown in Table 4.

Example 5

Immunochromatographic test strips were produced in the same manner as in Example 1 except that 0.6 mL of an aqueous solution containing N-acetoxysuccinimide was applied instead of the aqueous solution containing phthalimide to the entire pad of the organic acid etc.—containing member (7), and the accelerated stability test was conducted. The results are shown in Table 4.

Example 6

Immunochromatographic test strips were produced in the same manner as in Example 1 except that 0.6 mL of an aqueous solution containing hydantoin was applied instead of the aqueous solution containing phthalimide to the entire pad of the organic acid etc.—containing member (7), and the accelerated stability test was conducted. The results are shown in Table 4.

TABLE 4

| Example | Organic Acid or Organic Acid Derivative | Incubation Period | | |
|---|---|---|---|---|
| | | 0 hour | 2 weeks | 4 weeks |
| 2 | N-acetylphthalimide | + | + | − |
| 3 | N-(tert-butoxycarbonyl-oxy)phthalimide | ++ | + | − |
| 4 | N-hydroxysuccinimide | + | ± | − |
| 5 | N-acetoxysuccinimide | + | + | + |
| 6 | hydantoin | ++ | + | ± |

The organic acids and the organic acid derivatives of Examples 2 to 6 are all compounds represented by the formula (1). In all of the Examples, the positive analyte could be detected even after two weeks of incubation at 50° C., and it was found that the storage stability was high. In particular, in Example 5 (N-acetoxysuccinimide) and Example 6 (hydantoin), the positive analyte could be detected even after four weeks of incubation at 50° C., and it was found that the storage stability was especially high.

Although the present invention has been explained in detail using specific embodiments, it is obvious to one skilled in the art that various changes and modifications can be made without departing from the intention and the scope of the present invention. The present application is based on a Japanese patent application filed on Mar. 4, 2016 (patent application No. 2016-042707), which is hereby incorporated by reference in its entirety.

REFERENCE SIGNS LIST

1. Sample droplet-receiving member
11. Sample droplet-receiving part
2. Labeling substance-holding member
21. Labeling substance-containing part
3. Chromatography medium member
4. Detection part
5. Absorption member
6. Backing sheet
7. Organic acid etc.—containing member
A, B, C. Member
a. Part containing nitrous acid compound
b. Part containing organic acid or the like

The invention claimed is:

1. An immunochromatographic device for detecting a detection target in an analyte which comprises a sample droplet-receiving member, a labeling substance-holding member having a labeling substance-containing part, a chromatography medium member having a detection part and an absorption member and which contains a nitrous acid compound and an organic acid or an organic acid derivative, wherein the sample droplet-receiving member, the labeling substance-holding member, the chromatography medium member and the absorption member are arranged in a manner that a sample develops in this order, the immunochromatographic device has a part containing the nitrous acid compound and a part containing the organic acid or the organic acid derivative at upstream positions from the labeling substance-containing part, and the part containing the nitrous acid compound and the part containing the organic acid or the organic acid derivative are not substantially in contact with each other in the thickness direction wherein the organic acid or the organic acid derivative is a nitrogen-containing heterocyclic compound represented by the following formula (1),

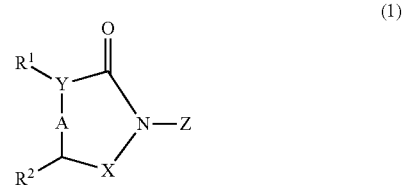

(1)

wherein in the formula (1), $R^1$ and $R^2$ each independently represents a hydrogen atom, a carbonyl group or an alkyl group which may have a substituent, wherein alkyl groups may bind to each other to form a ring and form an alicyclic hydrocarbon ring or an aromatic hydrocarbon ring, A represents a single bond or a double bond, X represents —C(=O)— or —(CH$_2$)$_n$—, Y represents a carbon atom or a nitrogen atom, n is 1 or 2, and Z represents a hydrogen atom, a hydroxyl group, an alkyl group which may have a substituent, —C(=O)R$^3$ or —O—C(=O)R$^3$, wherein R$^3$ represents an alkyl group which may have a substituent or an alkoxy group.

2. The immunochromatographic device according to claim 1, wherein the organic acid or the organic acid derivative is at least one selected from the group consisting of phthalimide, N-acetylphthalimide, N-(tert-butoxycarbonyloxy)phthalimide, N-hydroxysuccinimide, N-acetoxysuccinimide and hydantoin.

3. The immunochromatographic device according to claim 1, wherein the nitrous acid compound is a nitrite.

4. The immunochromatographic device according to claim 1, wherein the detection target is a Gram-positive bacterium.

5. The immunochromatographic device according to claim 4, wherein the Gram-positive bacterium is a hemolytic *Streptococcus*.

* * * * *